United States Patent
Gao et al.

(10) Patent No.: US 11,921,097 B2
(45) Date of Patent: Mar. 5, 2024

(54) METHOD FOR DYNAMIC MEASUREMENT OF INDIVIDUAL TREE CARBON SINK

(71) Applicants: Sichuan Provincial Institute of Forestry and Grassland Inventory and Planning, Sichuan (CN); Sichuan Yangdi Shikong Technology Co., Ltd, Sichuan (CN)

(72) Inventors: Fei Gao, Sichuan (CN); Nana Li, Sichuan (CN)

(73) Assignees: Sichuan Provincial Institute of Forestry and Grassland Inventory and Planning, Chengdu (CN); Sichuan Yangdi Shikong Technology Co., Ltd, Chengdu (CN)

( * ) Notice: Subject to any disclaimer, the term of this patent is extended or adjusted under 35 U.S.C. 154(b) by 0 days.

(21) Appl. No.: 18/219,111

(22) Filed: Jul. 7, 2023

(65) Prior Publication Data
US 2024/0019412 A1    Jan. 18, 2024

(30) Foreign Application Priority Data
Jul. 13, 2022    (CN) .......................... 202210822181.0

(51) Int. Cl.
| | | |
|---|---|---|
| G01D 21/02 | (2006.01) | |
| G01N 33/00 | (2006.01) | |
| G01N 33/02 | (2006.01) | |

(52) U.S. Cl.
CPC .............................. *G01N 33/0098* (2013.01)

(58) Field of Classification Search
CPC ......... G01D 21/02; Y02P 90/80; Y02P 90/84; Y02P 60/20; G06N 3/006; G06N 3/088; H04W 4/38; G01N 33/24
(Continued)

(56) References Cited

U.S. PATENT DOCUMENTS

| | | | | |
|---|---|---|---|---|
| 11,615,428 B1* | 3/2023 | Joseph | ................. | G06Q 30/018 705/317 |
| 2007/0073604 A1* | 3/2007 | Millen, II | .............. | G06Q 40/00 705/35 |

(Continued)

FOREIGN PATENT DOCUMENTS

| | | |
|---|---|---|
| CN | 104820065 A | 8/2015 |
| CN | 204536307 U | 8/2015 |

(Continued)

OTHER PUBLICATIONS

Notice of First Office Action of counterpart Chinese Patent Application No. 202210822181.0 dated Aug. 19, 2022.
(Continued)

*Primary Examiner* — Jeffrey P Aiello (57) ABSTRACT

A method for dynamic measurement of individual tree carbon sink, including: 1. Individual tree survey and equipment arrangement; 2. Automatic data collection of individual tree; 3. Computation of individual tree carbon sink: computing height, volume, biomass, and carbon storage of an individual tree by using the data collected in step 2; 4. Detecting state changes of an individual tree, and performing step 6 if it changes, otherwise performing step 5; 5. Continuous monitoring of individual tree carbon sink: continuously receiving the data collected in step 2 at set monitoring frequency and performing step 3, while storing the data; 6. Verification on the monitoring state of the individual tree. The invention can reduce erroneous measurements, repeated measurements, data fabrication, missing measurements, data recording and computation errors, and the workload of quality control and continuous monitoring, realizing continuous and accurate monitoring of individual tree carbon sink, and significantly improve monitoring timeliness.

7 Claims, 8 Drawing Sheets

(58) Field of Classification Search
USPC .......... 47/DIG. 6; 382/110, 103; 702/2, 188, 702/19, 179, 183, 62, 23, 182, 1, 127, 702/187, 3, 33; 703/2, 11
See application file for complete search history.

(56) References Cited

U.S. PATENT DOCUMENTS

| 2014/0019179 | A1 | 1/2014 | Gosalvez et al. |
| 2023/0078852 | A1* | 3/2023 | Campbell ............... G06F 16/29 705/7.11 |

FOREIGN PATENT DOCUMENTS

| CN | 105319322 | A | | 2/2016 | |
| CN | 110245420 | A | | 9/2019 | |
| CN | 111340644 | A | | 6/2020 | |
| CN | 113705015 | A | | 11/2021 | |
| CN | 114463403 | A | | 5/2022 | |
| CN | 115082273 | A | * | 9/2022 | |
| WO | WO-2011014782 | A1 | * | 2/2011 | ......... G01N 33/0004 |

OTHER PUBLICATIONS

Notice of Allowance of counterpart Chinese Patent Application No. 202210822181.0 dated Aug. 30, 2022.
Chunming Yan, Calculation and value evaluation of forest carbon sink in Zhangye Forest Park, Forestry Science and Technology, Mar. 2018, pp. 60-62.
Pai Peng et al., Construction of single plant growth model of four coniferous low-efficiency forests, Hunan Forestry Science & Technology, Dec. 2016, pp. 34-39, vol. 43, No. 6.
Zhou Lin, Study on carbon metering model, prediction and application of Chinese fir in Fujian Province at different scales, The Thesis of Fujian Agriculture and Forestry University's Doctoral Student, 2016, Fujian Agriculture and Forestry University (FAFU).

* cited by examiner

METHOD FOR DYNAMIC MEASUREMENT OF INDIVIDUAL TREE CARBON SINK

CROSS REFERENCE TO RELATED APPLICATIONS

The present application claims the benefit of Chinese Patent Application No. 202210822181.0 filed on Jul. 13, 2022, the contents of which are incorporated herein by reference in their entirety.

FIELD OF THE INVENTION

The present invention belongs to the field of data collection, computation, and processing technologies for the Internet of things, and specifically relates to a method for dynamic measurement of individual tree carbon sink.

BACKGROUND OF THE INVENTION

A scientific, reasonable, and easy-to-operate carbon sink measurement methodology is the foundation for carbon sink monitoring, reporting, and verification. The carbon sink measurement method based on individual trees helps to lower the threshold for public participation in carbon inclusion, and promotes and guides the public and small and micro enterprises to join in energy conservation and carbon reduction actions. At present, Guizhou Province has released the Methodology for Individual Tree Carbon Sink Projects in Guizhou Province and established individual tree carbon sink platform in Guizhou Province to carry out carbon sink trading. Liuzhou City, Guangxi Province, has released the Methodology for Individual Tree Carbon Sink Measurement and launched a carbon sink targeted ecological poverty alleviation project to build a carbon sink trading platform. However, due to the difficulties in actual measurement and monitoring, the individual tree carbon sink in Guizhou Province is 3 yuan per tree, which is not computed according to the published methodology; and diameters of trees at breast heights are manually determined in Liuzhou City.

The measurement and trading of individual carbon sink have the following shortcomings:

Measurement costs are high and erroneous measurements easily occur. Individual tree carbon sink measurement needs to complete field measurement, photography, listing, registration, and computation processes to obtain carbon sink. Professional investigators are required for the field measurement, which may lead to inaccurate data due to measurement errors and data entry and operation errors.

Data may be fabricated off site. Because quality control in forestry investigations is mainly based on spot checks, some investigators in fluke mind start field surveys without arriving at designated tree locations, or even fabricate data entirely indoors.

The workload of quality control is heavy. Inspectors need to inspect and compute each tree again according to an original investigation method, resulting in heavy workload of quality control. The quality control repeats an investigation process, and scales and computes standing trees repeatedly, resulting in high work costs and repeated content.

The monitoring timeliness is poor, and the data are static. Detailed growth dynamics of trees cannot be accurately grasped due to the heavy workload and high cost of a single field survey and poor monitoring timeliness, and the carbon sink of trees is closely related to and dynamically changes with tree growth. Changes in trees cannot be discovered in a timely manner. Whether trees exist and whether significant changes have occurred can be discovered only by another field survey, so monitoring plans cannot be adjusted in a timely manner.

In summary, a method for dynamic measurement of individual tree carbon sink is urgently required to reduce erroneous measurements, repeated measurements, and data fabrication in individual tree carbon sink measurement processes, reduce probabilities of missing measurements and data recording and computation errors, significantly reduce the workload of quality control and continuous monitoring, implement continuous and accurate monitoring of individual tree carbon sink, and significantly improve monitoring timeliness.

SUMMARY OF THE INVENTION

The objective of the present invention is to provide a method for dynamic measurement of individual tree carbon sink, which can reduce erroneous measurements, repeated measurements, and data fabrication in individual tree carbon sink measurement processes, reduce probabilities of missing measurements, data recording, and computation errors, significantly reduce the workload of quality control and continuous monitoring, implement continuous and accurate monitoring of an individual tree carbon sink, and significantly improve monitoring timeliness.

The above objective is achieved through the following technical solution: a method for dynamic measurement of individual tree carbon sink includes the following steps:

(1) individual tree survey and equipment arrangement;
(2) automatic data collection of individual tree:
(3) computation of individual tree carbon sink: computing the height, volume, biomass, and carbon storage of an individual tree by using the data collected in step (2);
(4) detecting state changes of an individual tree, and performing step (6) if the monitoring state of the individual tree changes, otherwise performing step (5);
(5) continuous monitoring of the individual tree carbon sink: continuously receiving the data collected in step (2) at the set monitoring frequency and performing step (3), while storing the data;
(6) verification on the monitoring state of the individual tree: verifying the state of the individual tree on site, determining on site whether the monitoring state of the individual tree changes due to equipment reasons or the state of the individual tree changes, and performing step (1) if the monitoring state of the individual tree changes due to equipment reasons and the monitoring continues, or ending the process if the state of the individual tree changes or the monitoring does not continue.

According to a further technical solution, in step (1), a target individual tree is first surveyed, survey factors are filled in, a communication relay device and a tree diameter measuring sensor for measuring a diameter of a tree are arranged, a data collection terminal is connected to the tree diameter measuring sensor through communication, and the tree diameter measuring sensor is connected to the communication relay device through communication; and in step (2), survey data are transmitted and entered into the communication relay device.

According to a further technical solution, specific steps of step (5) are as follows:

(5.1) the communication relay device is regularly started according to the set wake-up time;

(5.2) the communication relay device accesses a network server on a server side to obtain the next wake-up time and wake-up duration;

(5.3) the tree diameter measuring sensor is regularly started according to the set wake-up time;

(5.4) the tree diameter measuring sensor measures the diameter at breast height of the target individual tree to obtain a measured value;

(5.5) the tree diameter measuring sensor is connected to the communication relay device to transmit information about the diameter at breast height, tilt angle and battery capacity of the target individual tree; (5.6) the tree diameter measuring sensor synchronizes in clock with the communication relay device to obtain the next wake-up time and wake-up duration, and enters a sleep state after success;

(5.7) the communication relay device receives data from the tree diameter measuring sensor for storage, and computes differences from previous measured data;

(5.8) the communication relay device computes a carbon storage variation according to the difference in tree diameter and stores the data;

(5.9) the communication relay device stores its own sensor data;

(5.10) the communication relay device transmits the stored information back to a communication receiving device and summarizes the information into the network server on the server side;

(5.11) a compute server on the server side obtains data from the network server and summarizes carbon sink variations of individual trees for visual display;

(5.12) the server side configures the wake-up time and wake-up duration of the communication relay device and the tree diameter measuring sensor.

According to a further technical solution, specific steps of step (3) are as follows:

(3.1) computing the height of the target individual tree by using a tree height curve of current tree species in a local region, with the diameter at breast height as an independent variable and the tree height as a dependent variable;

(3.2) computing the biomass of the target individual tree: performing step (3.3) if an allometric growth equation method is used, or performing step (3.5) if a biomass expansion factor method is used;

(3.3) computing the biomass by using an allometric growth equation, with the diameter at breast height and the tree height as independent variables and the biomass as a dependent variable, where a computational formula is as follows:

$$W=a(D^2H)^b$$

where W is the biomass of the target individual tree, H is the height of the target individual tree, D is the diameter of the target individual tree, a and b are coefficients;

(3.4) computing the volume of the target individual tree by using a binary volume table for the local region, with the diameter at breast height and the tree height as independent variables and the volume as a dependent variable, where a computational formula is as follows:

$$V=aD^bH^c$$

where V is the volume of the target individual tree, H is the height of the target individual tree, D is the diameter of the target individual tree, and a, b, and c are coefficients;

(3.5) computing the biomass by using the biomass expansion factor method, with the volume as an independent variable and the biomass as a dependent variable, and looking up tables to obtain three default data, namely, a wood density, a root-crown ratio, and a biomass expansion factor, where a computational formula is as follows:

$$W=V \times WD \times BEF \times (1+R)$$

where WD is the wood density of the target individual tree, BEF is the dimensionless biomass expansion factor that converts trunk biomass of the target individual tree to aboveground biomass, and R is the root-crown ratio of the target individual tree;

(3.6) converting forest biomass into the carbon storage by using the carbon content of forest biomass, and converting the carbon storage into a carbon dioxide equivalent, where a computational formula is as follows:

$$C_s=(44/12) \times W \times CF$$

where $C_s$ is the carbon storage of the target individual tree, and CF is the carbon content of the target individual tree.

According to a further technical solution, in step (4), if the communication relay device cannot receive measured data from the data measuring sensor, it is determined that the monitoring state of the individual tree has changed.

According to a further technical solution, specific steps of step (6) are as follows:

(6.1) reaching around the target individual tree, searching for the target individual tree according to survey information and a number plate, and performing step (6.2) if the target individual tree is found, or filling in reasons for the change in the monitoring state of the individual tree at the data collection terminal if the target individual tree is not found, and ending the process;

(6.2) searching for and starting a communication gateway, filling in equipment reasons at the data collection terminal and performing steps (1) and (2) if the communication gateway is not found or fails to start, or performing step (6.3) if the state of the communication gateway is normal;

(6.3) searching for the target individual tree, filling in equipment reasons at the data collection terminal, installing a new tree diameter measuring sensor on the trunk of the target individual tree, and performing step (2).

According to a further technical solution, the data collection terminal and the server side are deployed with a data collection application system and a system for dynamic measurement of an individual tree carbon sink, where the data collection application system is configured to obtain server side information, connect the communication relay device and the tree diameter measuring sensor in a survey field to collect, enter and compute data, and manage configurations of the communication relay device and the tree diameter measuring sensor; and the system for dynamic measurement of an individual tree carbon sink is configured for a manager to collect, count and visually analyze individual tree survey data obtained by the data collection terminal, and to manage parameter settings and operating states of all individual tree survey devices.

According to a further technical solution, the system for dynamic measurement of individual tree carbon sink includes:

a user login module: configured to log in to the system for dynamic measurement of individual tree carbon sink;

an individual tree map display, browse and query module: configured to provide interactive modes based on map operations and provide map operation functions including translation, zoom in, zoom out, hierarchical display, individual tree attribute information query, and individual tree coordinate positioning;

a survey table and default data configuration module: configured to configure a field tree survey attribute table, the tree height curve, the binary volume table, and default data;

a communication relay device equipment and state management module: configured to query an equipment number, equipment type and coordinate position of the communication relay device and number information of a sample plot, view the operating state, battery capacity and sensor measured data of the communication relay device, and configure the monitoring frequency, the wake-up time and wake-up duration for the communication relay device;

a tree diameter measuring sensor equipment and state management module: configured to query an equipment number of the tree diameter measuring sensor and number information of individual trees, view the operating state, battery capacity and sensor measured data of the tree diameter measuring sensor, and configure the wake-up time and wake-up duration for the tree diameter measuring sensor;

an individual tree carbon storage summarization and computation module: configured to summarize the data of the tree diameter measuring sensor transmitted back by each communication relay device through the receiving device, and compute a carbon storage result of an individual tree by using the tree height curve, the binary volume table, and the default data;

a carbon storage variation analysis module: configured to collect statistics on the summarized and computed individual tree data, analyze survey accuracy and carbon sink quantity, quality, structure and distribution output by region and type, and compare statuses of each monitoring object before and after a monitoring cycle, including output growth, consumption, and dynamic changes;

a carbon sink measurement result visual display module: configured to display monitoring data by using three-dimensional maps, visual charts, and time series axes, to intuitively reflect dynamic changes of monitoring results.

According to a further technical solution, the data collection application system includes:

a user login module: configured to log in to the data collection application system;

a map operation and positioning, navigation, track, and photography module: configured to provide interactive modes based on map operations and provide map operation functions including translation, zoom in, zoom out, hierarchical display, positioning, navigation, track collection, and photography;

a survey table and default data download module: configured to download and update the field tree survey attribute table, the tree height curve, the binary volume table, and the default data;

an individual tree field survey factor entry module: configured to enter basic information of project owners, project leaders and contacts, basic information of a project, basic information of a project forest land, and technical data information of the forest land;

a mobile communication signal testing module: configured to measure a type and strength of mobile signals in the survey field and communicate with a communication receiving end to test a success rate of signal transmission;

a communication relay device connection, testing and configuration module: configured to connect the data collection terminal with the communication relay device, set a data collection frequency, determine the start-up time and start-up duration of the communication relay device and the tree diameter measuring sensor;

a tree diameter measuring sensor connection and data entry module: configured to connect the data collection terminal with the tree diameter measuring sensor and enter tree species of surveyed trees, a forest ownership certificate number, and forest area information after confirming a correct connection;

a tree diameter measuring sensor and communication relay device data transmission module: configured to trigger a background communication event between the tree diameter measuring sensor and the communication relay device after the information of the surveyed trees is entered, and transmit the equipment number, tree species, forest ownership certificate number, and forest area information from the tree diameter measuring sensor to the communication relay device through a wireless communication module for storage;

an individual tree carbon sink measurement module: configured for a user to obtain tree survey data and then compute carbon storage by using the tree height curve, the binary volume table, and the default data. The computations include diameter at breast height, tree height, volume, biomass, and carbon storage.

Compared with the prior art, the technical solution of the present invention has the following advantages:

Erroneous and repeated measurements are avoided and missing measurements are unlikely to occur: when each tree is surveyed, the diameter of the tree is automatically measured by the tree diameter measuring sensor, and measurement personnel are not required for reading, so erroneous measurements are avoided; the measured standing tree is bound with the tree diameter measuring sensor to reduce repeated measurements; and the tree diameter measuring sensor marks the measured or unmeasured standing tree to greatly reduce the possibility of missing measurements.

Probabilities of data recording and computation errors are reduced: for continuous monitoring, data are automatically collected, data entry is not required, and computations are performed through software reuse, thereby reducing the probabilities of data recording and computation errors.

Data fabrication is reduced: forest data are required to be connected and transmitted to the network server on the server side, and the communication relay device has a GPS or Beidou RNSS module for positioning a sample plot, which ensures that the investigator has to arrive at the designated target individual tree before survey; and the equipment is bound before obtaining data, thereby reducing data fabrication.

Workload of quality control is greatly reduced: after arriving at the target individual tree, quality control personnel only need to check whether a sample tree is bound with equipment and whether the tree species is correct, and do not need to further measure each tree, thereby greatly reducing the workload of quality control.

Workload of continuous monitoring is greatly reduced: carbon storage and carbon storage variation data of the target individual tree can be stably obtained off site for continuous monitoring in the present invention, and computation and display are directly performed on the server side, thereby greatly reducing the workload of continuous monitoring.

Accuracy of continuous monitoring for a diameter at breast height is high: the tree diameter measuring sensor is bound to a fixed position all the time, so each measurement is at the same position, and inconsistency in the measurement position and diameter tape measurement errors do not occur.

Monitoring timeliness is greatly improved: the monitoring frequency in the present invention is determined by task requirements and battery capacity, and due to the use of low-power design and measurement once a day, the equipment works back once a week for 10 years, so the service life is significantly prolonged, and growth dynamics and carbon sink variations of trees can be accurately grasped.

Changes in the sample plot can be discovered in a timely manner: when the sample plot changes due to operating activities or natural disasters, changes in the target individual tree and time of the changes can be discovered through back transmission of data, and monitoring plans can be adjusted in a timely manner according to the changes.

BRIEF DESCRIPTION OF THE DRAWINGS

The accompanying drawing constituting a part of the present invention is used for providing a further understanding of the present invention, and the schematic embodiments of the present invention and the descriptions thereof are used for interpreting the present invention, rather than constituting improper limitations to the present invention.

DETAILED DESCRIPTION OF THE EMBODIMENTS

The present invention is described in detail below with reference to the accompanying drawings. The description in this section is only exemplary and explanatory, and should not have any limiting effect on the scope of protection of the present invention. In addition, those skilled in the art may combine embodiments and features in different embodiments correspondingly according to the description in this specification.

Figure 1:
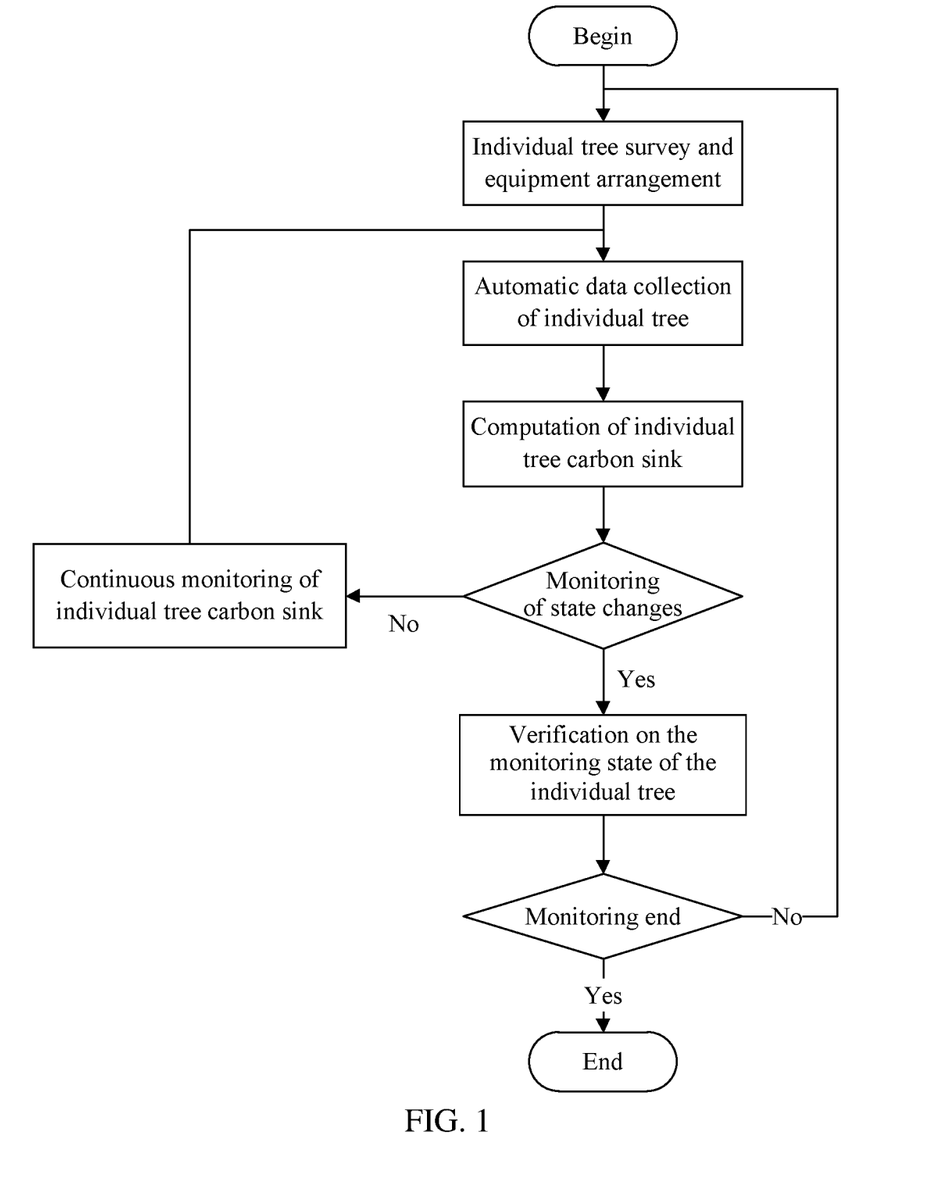
FIG. 1 is a flowchart of a method for dynamic measurement of individual tree carbon sink according to an embodiment of the present invention.
Figure 2:
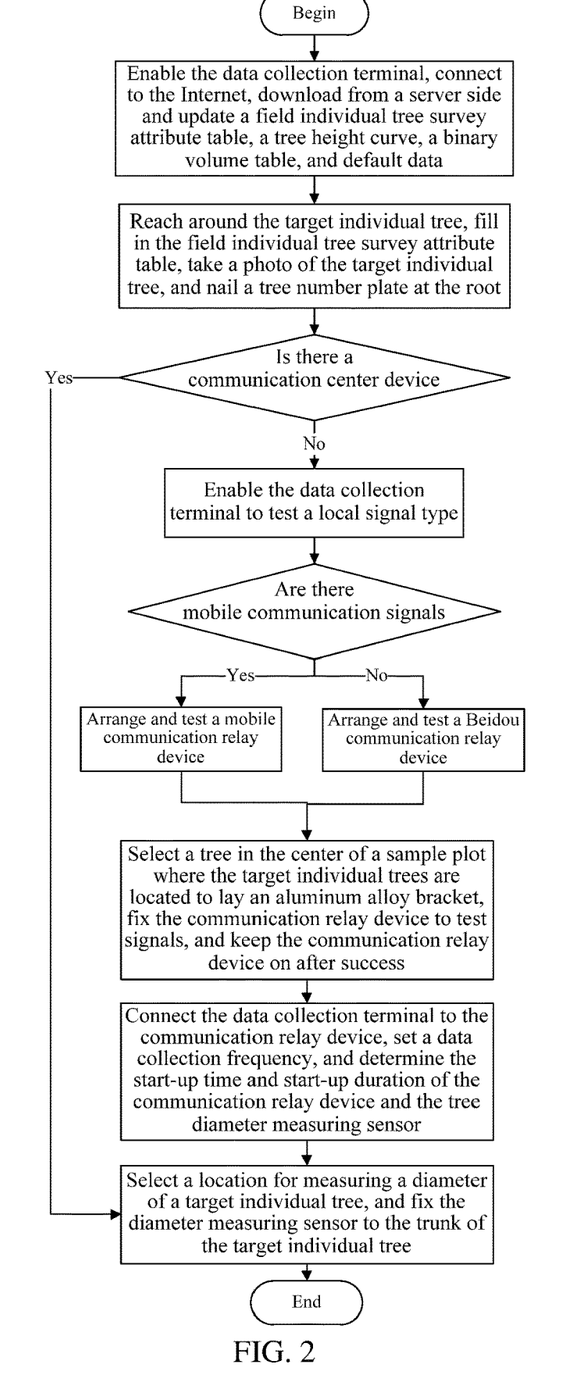
FIG. 2 is an operation flowchart of individual tree survey and equipment arrangement according to an embodiment of the present invention.

The embodiments of the present invention are as follows. With reference to FIG. 1, a method for dynamic measurement of individual tree carbon sink includes the following steps:

(1) Individual tree survey and equipment arrangement: a target individual tree is first surveyed, survey factors are filled in, a communication relay device and a tree diameter measuring sensor for measuring a diameter of a tree are arranged, a data collection terminal is connected to the tree diameter measuring sensor through communication, and the tree diameter measuring sensor is connected to the communication relay device through communication. Specific steps are shown in FIG. 2 as follows:

(1.1) The data collection terminal is enabled and connected to the Internet, and a field individual tree survey attribute table, a tree height curve, a binary volume table, and default data are downloaded from a server side and updated. The default data include but are not limited to a wood density, a biomass expansion factor, a root-crown ratio, and carbon content;

(1.2) Reach around the target individual tree, fill in the field individual tree survey attribute table, take a photo of the target individual tree, and nail a tree number plate at the root;

(1.3) Whether there is already a connectable communication relay device, and if so, step (1.7) is performed, otherwise step (1.4) is performed;

(1.4) The data collection terminal is enabled to test a local signal type, and a type of the communication relay device is selected according to a local communication status and distribution of target individual trees. A mobile communication relay device is selected for 2/3/4/5G mobile operator signals, or a Beidou communication relay device is selected for non-mobile operator signals;

(1.5) A tree is selected in the center of a sample plot where the target individual trees are located to lay an aluminum alloy bracket, the communication relay device is fixed to test signals, and the communication relay device is kept on after success;

(1.6) The data collection terminal is connected to the communication relay device, a data collection frequency is set, and the start-up time and start-up duration of the communication relay device and the tree diameter measuring sensor are determined;

(1.7) A location for measuring a diameter at breast height of a target individual tree is selected, and the diameter measuring sensor is fixed to the trunk of the target individual tree.

Figure 3:
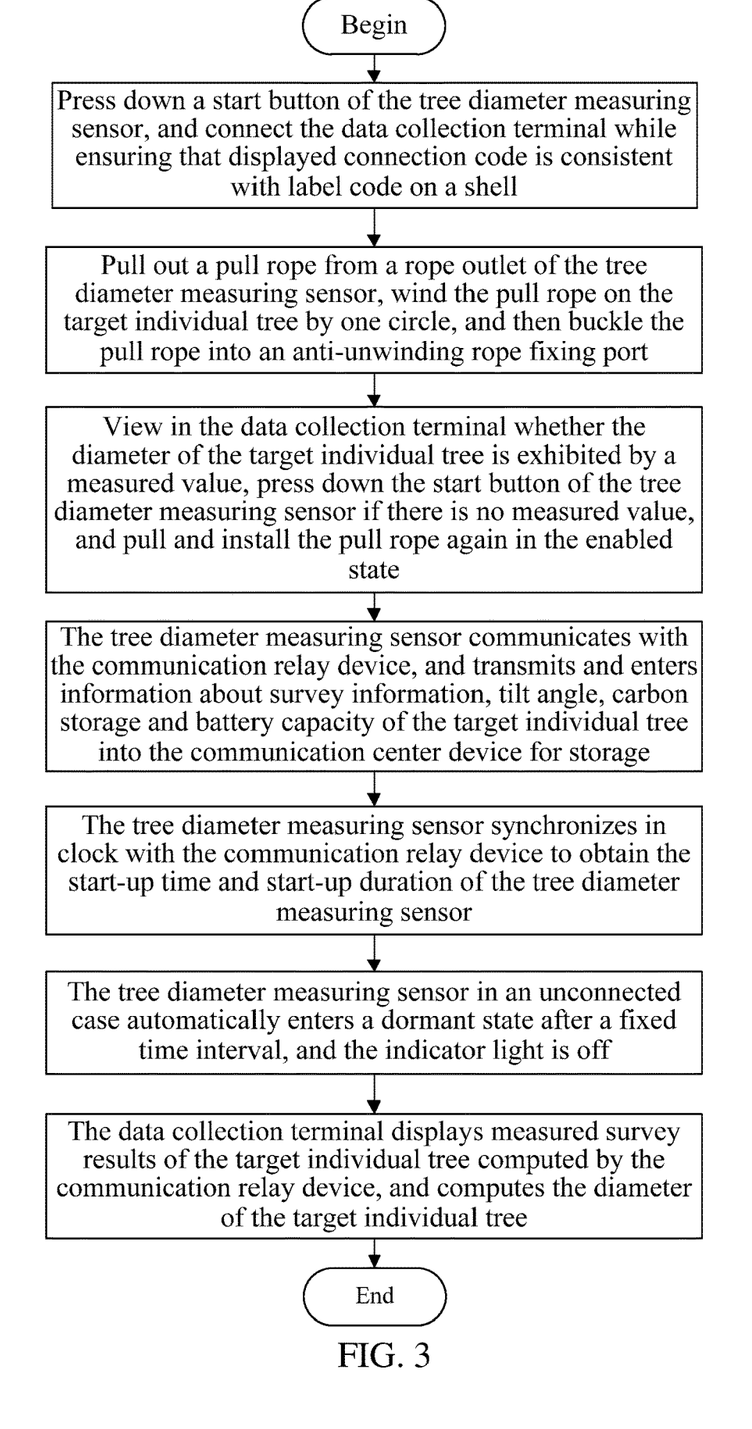
FIG. 3 is a schematic flowchart of automatic data collection of individual tree according to an embodiment of the present invention.

(2) Individual tree data are automatically collected, and survey data are transmitted and entered to the communication relay device. Specific steps are shown in FIG. 3:

(2.1) A start button of the tree diameter measuring sensor is pressed down, an indicator light is red, and the data collection terminal is connected to the tree diameter measuring sensor while ensuring that displayed code of the connected tree diameter measuring sensor is consistent with label code on a shell of the tree diameter measuring sensor.

(2.2) A pull rope is pulled out from a rope outlet of the tree diameter measuring sensor, wound on the target individual tree by one circle, and then buckled into an anti-unwinding rope fixing port.

(2.3) The tree diameter measuring sensor is automatically connected to the communication relay device, the indicator light is green after successful connection, whether the diameter at breast height of the target individual tree is exhibited by a measured value is viewed in the data collection terminal, the start button of the tree diameter measuring sensor is pressed down if there is no measured value, and the pull rope is pulled and installed again in the enabled state.

(2.4) The tree diameter measuring sensor communicates with the communication relay device, and transmits and enters information about survey information, tilt angle, carbon storage and battery capacity of the target individual tree into a communication center device for storage.

(2.5) The tree diameter measuring sensor synchronizes in clock with the communication relay device to obtain the start-up time and start-up duration of the tree diameter measuring sensor.

(2.6) The tree diameter measuring sensor in an unconnected case automatically enters a sleep state after a fixed time interval, and the indicator light is turned off.

(2.7) The data collection terminal displays measured survey results of the target individual tree computed by the communication relay device, and computes the diameter at breast height of the target individual tree. The diameter at breast height of the target individual tree is directly measured and computed by the tree diameter measuring sensor, where a computational formula is as follows:

$$D=C/\pi$$

where C—the length of the pull rope of the tree diameter measuring sensor, and D—the diameter at breast height of the target individual tree.

Figure 4:
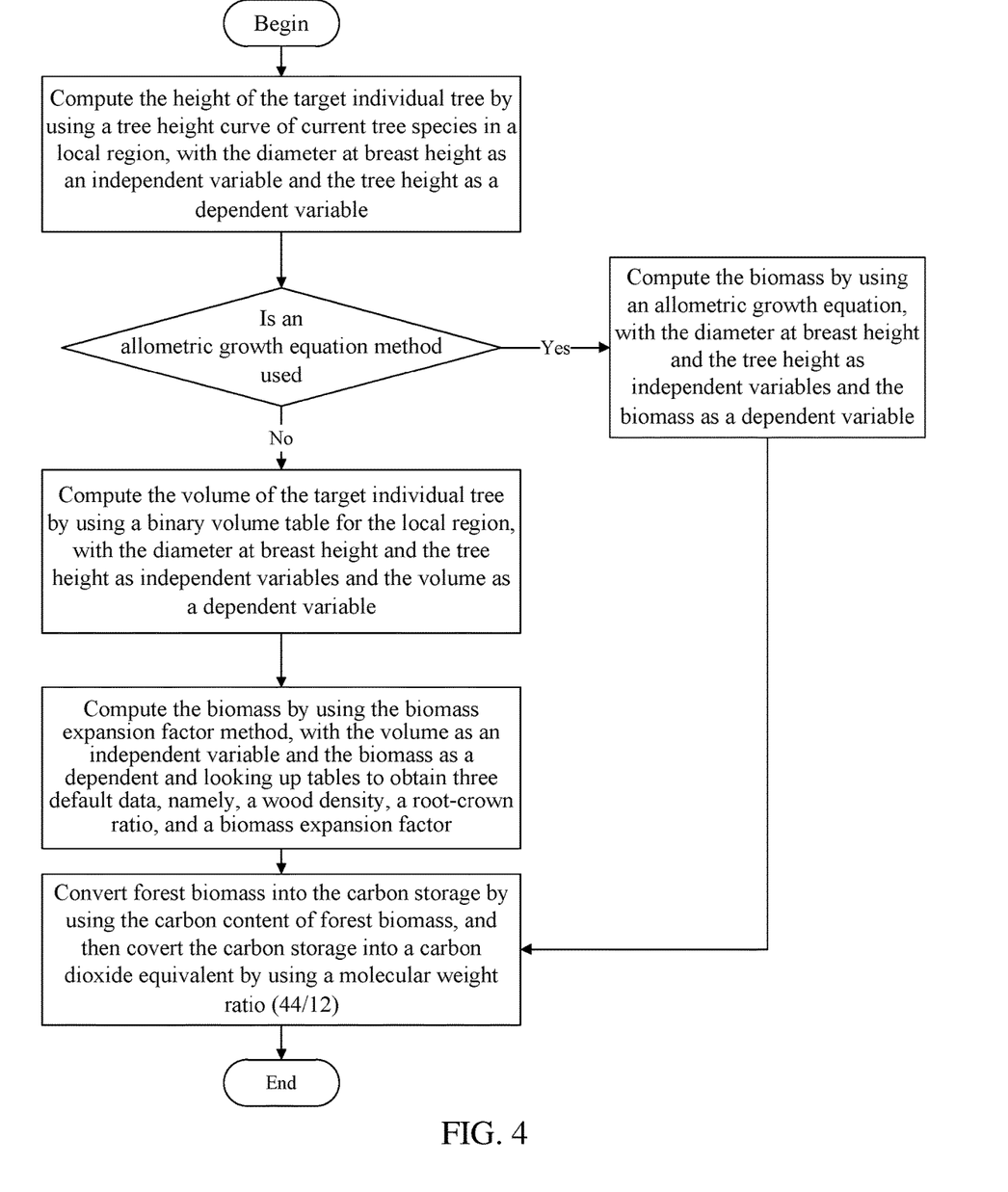
FIG. 4 is a schematic flowchart of computation of individual tree carbon sink according to an embodiment of the present invention.

(3) Computation of individual tree carbon sink: a height, volume, biomass, and carbon storage of an individual tree are computed by using the data collected in step (2).

Specific steps are shown in FIG. 4 as follows:

(3.1) The height of the target individual tree is computed by using a tree height curve of current tree species in a local region, with the diameter at breast height as an independent variable and the tree height as a dependent variable, where a computational formula is as follows:

$$H=a+bD+cD^2$$

where H is the height of the target individual tree; D is the diameter at breast height of the target individual tree; and a, b, and c are coefficients.

(3.2) The biomass of the target individual tree is computed: step (3.3) is performed if an allometric growth equation method is used, or step (3.5) is performed if a biomass expansion factor method is used;

(3.3) The biomass is computed by using an allometric growth equation, with the diameter at breast height and the tree height as independent variables and the biomass as a dependent variable, where a computational formula is as follows:

$$W=a(D^2H)^b$$

where W is the biomass of the target individual tree, H is the height of the target individual tree, D is the diameter of the target individual tree, a and b are coefficients;

(3.4) The volume of the target individual tree is computed by using a binary volume table for the local region, with the diameter at breast height and the tree height as independent variables and the volume as a dependent variable, where a computational formula is as follows:

$$V=aD^bH^c$$

where V is the volume of the target individual tree, H is the height of the target individual tree, D is the diameter of the target individual tree, and a, b, and c are coefficients;

(3.5) The biomass is computed by using the biomass expansion factor method, with the volume as an independent variable and the biomass as a dependent variable, and looking up tables to obtain three default data, namely, a wood density, a root-crown ratio, and a biomass expansion factor, where a computational formula is as follows:

$$W=V \times WD \times BEF \times (1+R)$$

where WD is the wood density of the target individual tree, BEF is the dimensionless biomass expansion factor that converts trunk biomass of the target individual tree to aboveground biomass, and R is the root-crown ratio of the target individual tree;

(3.6) Forest biomass is converted into the carbon storage by using the carbon content of forest biomass, and the carbon storage is converted into a carbon dioxide equivalent, where a computational formula is as follows:

$$C_s=(44/12) \times W \times CF$$

where $C_s$ is the carbon storage of the target individual tree, and CF is the carbon content of the target individual tree.

(4) State changes of an individual tree are detected, and step (6) is performed if the monitoring state of the individual tree changes, otherwise step (5) is performed.

Figure 5:
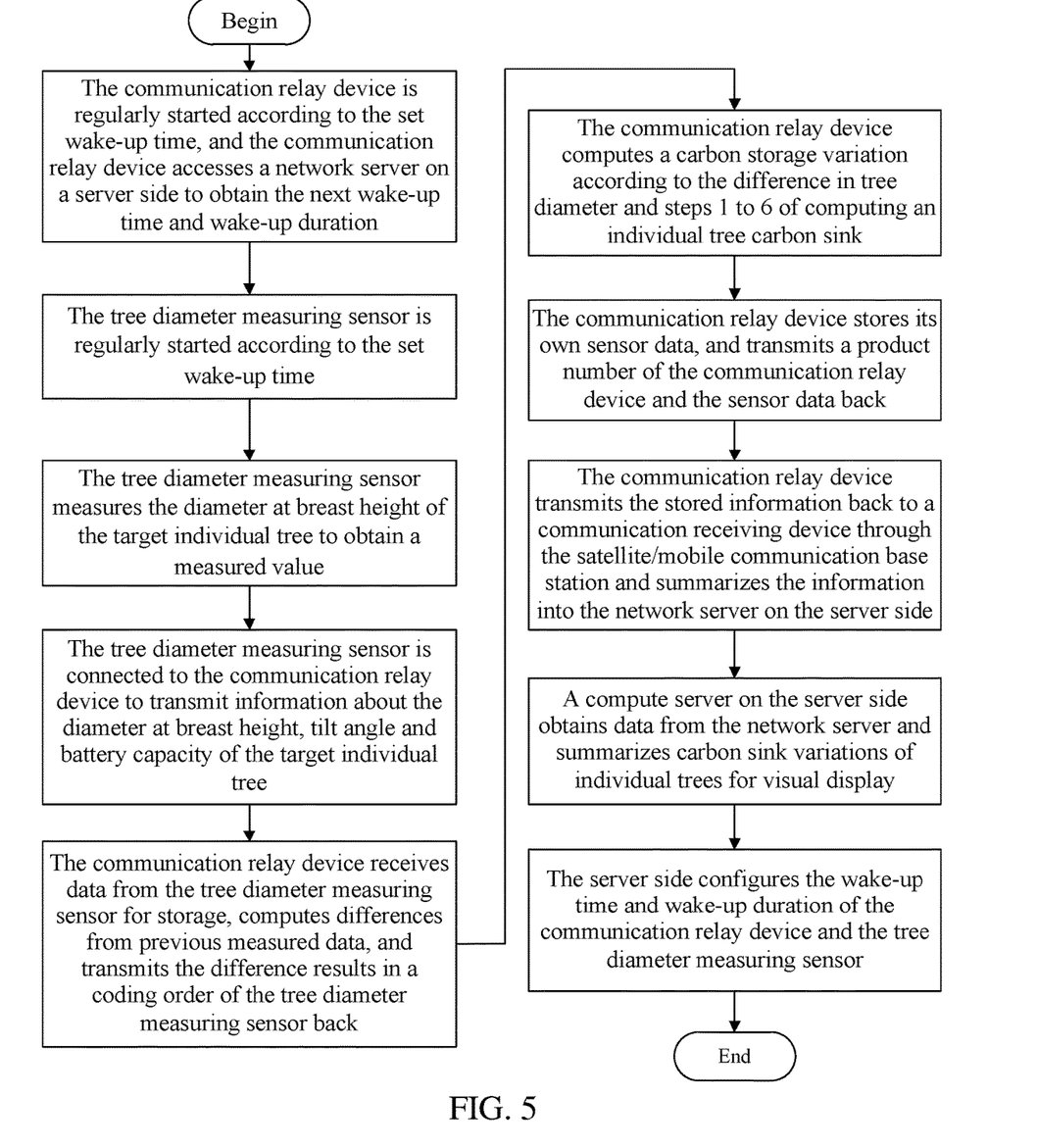
FIG. 5 is a schematic flowchart of continuous monitoring of the individual tree carbon sink according to an embodiment of the present invention.

(5) Continuous monitoring of the individual tree carbon sink: the data collected in step (2) is continuously received at a set monitoring frequency and step (3) is performed, while the data are stored.

Specific steps of step (5) are shown in FIG. 5 as follows:

(5.1) The communication relay device is regularly started according to the set wake-up time. Generally, the start-up time of the communication relay device is earlier than that of the tree diameter measuring sensor.

(5.2) The communication relay device accesses a network server on the server side through a satellite/mobile communication base station to obtain the next wake-up time and wake-up duration.

(5.3) The tree diameter measuring sensor is regularly started according to the set wake-up time.

(5.4) The tree diameter measuring sensor measures the diameter at breast height of the target individual tree to obtain a measured value.

(5.5) The tree diameter measuring sensor is connected to the communication relay device to transmit information about the diameter at breast height, tilt angle and battery capacity of the target individual tree.

(5.6) The tree diameter measuring sensor synchronizes in clock with the communication relay device to obtain next the wake-up time and wake-up duration, and enters a sleep state after success.

(5.7) The communication relay device receives data from the tree diameter measuring sensor for storage, computes differences from previous measured data, and transmits the difference results in a coding order of the tree diameter measuring sensor back. For the tree diameter measuring sensor that does not obtain a measured value, the difference is set to 9999.

(5.8) The communication relay device computes a carbon storage variation according to the difference in tree diameter and stores the data, where a computational formula is as follows:

$$\Delta C_S = C_{S_{t_2}} - C_{S_{t_1}}$$

where $\Delta C_s$—the carbon storage variation of the measured tree, $$C_{S_{t_2}}$$

—carbon storage of the measured tree at time $t_2$, and $$C_{S_{t_1}}$$

—carbon storage of the measured tree at time $t_1$.

(5.9) The communication relay device stores its own sensor data, and transmits a product number of the communication relay device and the sensor data back. The sensors of the communication relay device include but are not limited to a temperature sensor, a humidity sensor, and a tilt sensor, which monitor environmental factors of the measured individual tree.

(5.10) The communication relay device transmits the stored information back to a communication receiving device through the satellite/mobile communication base station and summarizes the information into the network server on the server side. The information transmitted back through the satellite is transmitted back to the Beidou director and summarized into the network server. The information transmitted back through the mobile communication base station is transmitted back to the communication server and summarized into the network server.

(5.11) A compute server on the server side obtains data from the network server and summarizes carbon sink variations of individual trees for visual display.

(5.12) The server side configures the wake-up time and wake-up duration of the communication relay device and the tree diameter measuring sensor.

Figure 6:
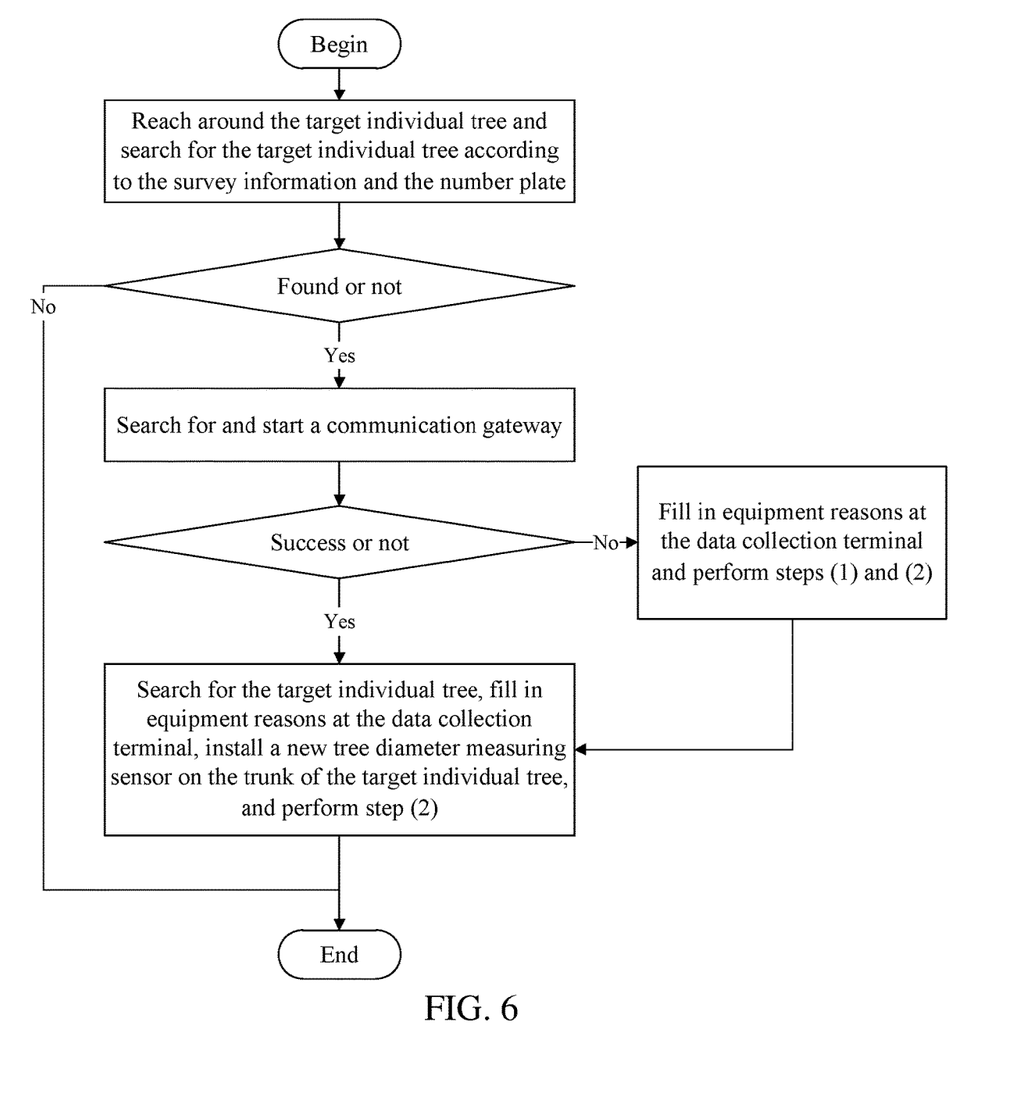
FIG. 6 is a flowchart of verification on the monitoring state of the individual tree according to an embodiment of the present invention.

(6) Verification on the monitoring state of the individual tree: the state of the individual tree is verified on site, whether the monitoring state of the individual tree changes due to equipment reasons or the state of the individual tree changes is determined on site, and step (1) is performed if the monitoring state of the individual tree changes due to equipment reasons and the monitoring continues, or the process ends if the state of the individual tree changes or the monitoring does not continue.

As shown in FIG. 6, specific steps of step (6) are as follows:

(6.1) Reaching around the target individual tree, and search the target individual tree according to the survey information and the number plate, and step (6.2) is performed if the target individual tree is found, or reasons for the change in the monitoring state of the individual tree are filled in at the data collection terminal if the target individual tree is not found, and the process ends.

(6.2) A communication gateway is searched and started, equipment reasons are filled in at the data collection terminal and steps (1) and (2) are performed if the communication gateway is not found or fails to start, or step (6.3) is performed if the state of the communication gateway is normal.

(6.3) The target individual tree is searched, equipment reasons are filled in at the data collection terminal, a new tree diameter measuring sensor is installed on the trunk of the target individual tree, and step (2) is performed.

On the basis of the foregoing embodiment, in another embodiment of the present invention, in step (4), if the communication relay device cannot receive measured data from the data measuring sensor, it is determined that the monitoring state of the individual tree has changed.

On the basis of the foregoing embodiments, in another embodiment of the present invention, the data collection terminal and the server side are deployed with a data collection application system and a system for dynamic measurement of individual tree carbon sink, where the data collection application system is configured to obtain server side information, connect the communication relay device and the tree diameter measuring sensor in a survey field to collect, enter and compute data, and manage configurations of the communication relay device and the tree diameter measuring sensor; and the system for dynamic measurement of individual tree carbon sink is configured for a manager to collect, count and visually analyze individual tree survey data obtained by the data collection terminal, and to manage parameter settings and operating states of all individual tree survey devices.

Figure 7:
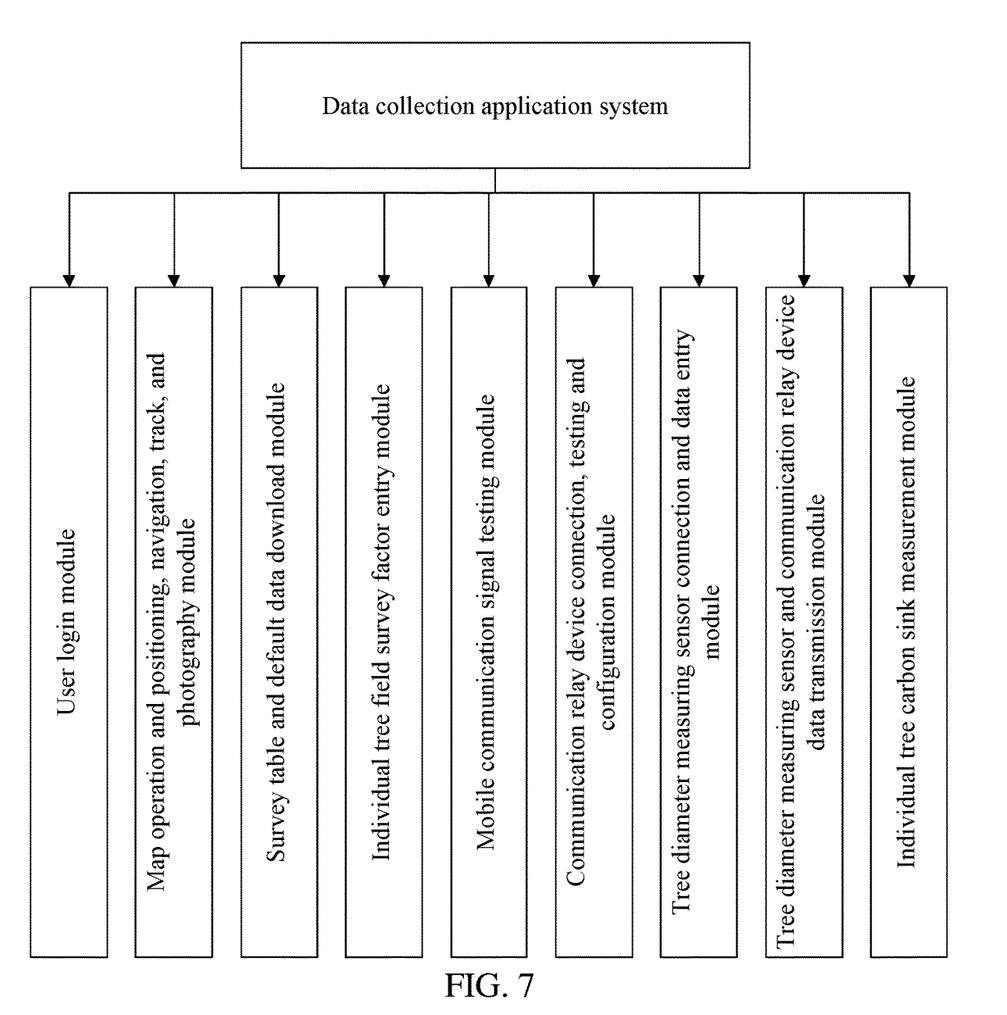
FIG. 7 is a structural block diagram of a system for dynamic measurement of individual tree carbon sink according to an embodiment of the present invention.

On the basis of the foregoing embodiments, in another embodiment of the present invention, as shown in FIG. 7, the system for dynamic measurement of individual tree carbon sink includes:

- a user login module: configured to verify a user identity and log in to the system for dynamic measurement of individual tree carbon sink;
- an individual tree map display, browse and query module: configured to provide interactive modes based on map operations for a user and provide basic map operation functions such as translation, zoom in, zoom out, and hierarchical display, and advanced map operation functions such as individual tree attribute information query and individual tree coordinate positioning;
- a survey table and default data configuration module: configured for the user to configure the field tree survey attribute table, the tree height curve, the binary volume table, and default data, where the default data include but are not limited to a wood density, a biomass expansion factor, a root-crown ratio, and carbon content;
- a communication relay device equipment and state management module: configured for the user to query an equipment number, equipment type and coordinate position of the communication relay device and number information of a sample plot, view the operating state, battery capacity and sensor measured data of the communication relay device, and configure the monitoring frequency, the wake-up time and wake-up duration for the communication relay device;
- a tree diameter measuring sensor equipment and state management module: configured for the user to query an equipment number of the tree diameter measuring sensor and number information of individual trees, view the operating state, battery capacity and sensor measured data of the tree diameter measuring sensor, and configure the wake-up time and wake-up duration for the tree diameter measuring sensor;
- an individual tree carbon storage summarization and computation module: configured for the user to summarize the data of the tree diameter measuring sensor transmitted back by each communication relay device through the receiving device, and compute a carbon storage result of an individual tree by using the tree height curve, the binary volume table, and the default data, where the computations include diameter at breast height, tree height, volume, biomass, and carbon storage;

a carbon storage variation analysis module: configured for the user to collect statistics on the summarized and computed individual tree data, analyze survey accuracy and carbon sink quantity, quality, structure and distribution output by region and type, and compare statuses of each monitoring object before and after a monitoring cycle, including output growth, consumption, and dynamic changes;

a carbon sink measurement result visual display module: configured for the user to display monitoring data by using three-dimensional maps, visual charts, time series axes, or the like, to intuitively reflect dynamic changes of monitoring results.

Figure 8:
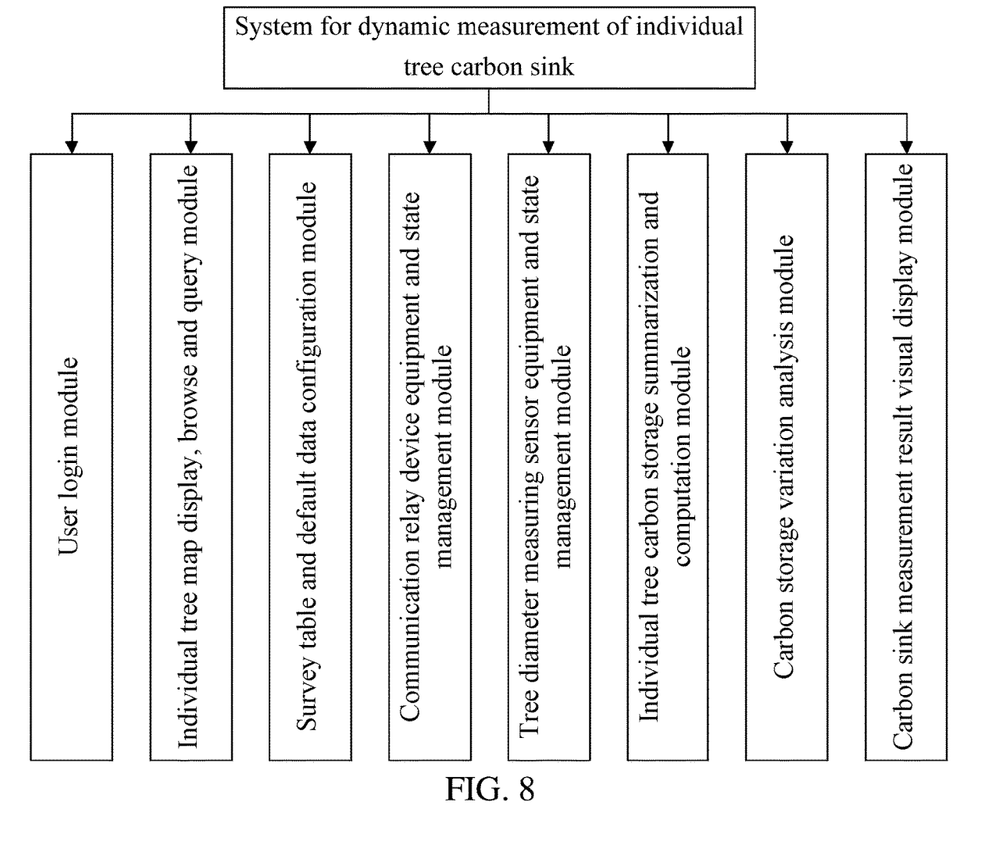
FIG. 8 is a structural block diagram of a data collection application system according to an embodiment of the present invention.

On the basis of the foregoing embodiments, in another embodiment of the present invention, as shown in FIG. 8, the data collection application system includes:

a user login module: configured to verify a user identity and log in to the data collection application system;

a map operation and positioning, navigation, track, and photography module: configured for the user to provide interactive modes based on map operations and provide basic map operation functions such as translation, zoom in, zoom out, and hierarchical display, and advanced map operation functions such as positioning, navigation, track collection, and photography;

a survey table and default data download module: configured for the user to download and update the field tree survey attribute table, the tree height curve, the binary volume table, and the default data, where the default data include but are not limited to a wood density, a biomass expansion factor, a root-crown ratio, and carbon content;

an individual tree field survey factor entry module: configured for the user to enter basic information of project owners, project leaders and contacts, basic information of a project, basic information of a project forest land, and technical data information of the forest land;

a mobile communication signal testing module: configured for the user to measure a type and strength of mobile signals in the survey field and communicate with a communication receiving end to test a success rate of signal transmission, where the user is prompted to select a mobile communication relay device for 2/3/4/5G mobile operator signals, or the user is prompted to select a Beidou communication relay device for non-mobile operator signals;

a communication relay device connection, testing and configuration module: configured for the user to connect the data collection terminal with the communication relay device, set a data collection frequency, determine the start-up time and start-up duration of the communication relay device and the tree diameter measuring sensor, where the module may estimate a theoretical monitoring time length according to the data collection frequency and battery capacity set by the user;

a tree diameter measuring sensor connection and data entry module: configured for the user to connect the data collection terminal with the tree diameter measuring sensor and enter tree species of surveyed trees, a forest ownership certificate number, and forest area information after confirming a correct connection;

a tree diameter measuring sensor and communication relay device data transmission module: configured for the user to trigger a background communication event between the tree diameter measuring sensor and the communication relay device after the information of the surveyed trees is entered, and transmit the equipment number, tree species, forest ownership certificate number, and forest area information from the tree diameter measuring sensor to the communication relay device through a wireless communication module for storage;

an individual tree carbon sink measurement module: configured for the user to obtain tree survey data and then compute carbon storage by using the tree height curve, the binary volume table, and the default data, where the computations include diameter at breast height, tree height, volume, biomass, and carbon storage.

Described above are merely preferred embodiments of the present invention. It should be pointed out that many improvements and modifications may also be made for those of ordinary skill in the art without departing from the principle of the present invention, and these improvements and modifications shall fall into the protection scope of the present invention.

What is claimed is:

1. A method for dynamic measurement of individual tree carbon sink, comprising following steps:
    (1) equipment arrangement: arranging a communication relay device and a tree diameter measuring sensor for measuring a diameter at breast height of a target individual tree, connecting a data collection terminal to the tree diameter measuring sensor through communication, and connecting the tree diameter measuring sensor to the communication relay device through communication;
    (2) automatically collecting individual tree data, and transmitting the individual tree data to the communication relay device;
    (3) computation of individual tree carbon sink: computing a height, a volume, a biomass, and a carbon storage of the target individual tree by using the data collected in step (2);
    (3.1) computing the height of the target individual tree by using a tree height curve of current tree species in a local region, with the diameter at breast height as an independent variable and the height as a dependent variable;
    (3.2) computing the biomass of the target individual tree: performing step (3.3) if an allometric growth equation method is used, and performing step (3.5) if a biomass expansion factor method is used;
    (3.3) computing the biomass by using an allometric growth equation, with the diameter at breast height and the height as independent variables and the biomass as a dependent variable, wherein a computational formula is as follows:

$$W = a(D^2 H)^b$$

where W is the biomass of the target individual tree, H is the height of the target individual tree, D is the diameter at breast height of the target individual tree, a and b are coefficients;

(3.4) computing the volume of the target individual tree by using a binary volume table for the local region, with the diameter at breast height and the height as independent variables and the volume as a dependent variable, wherein a computational formula is as follows:

$$V = aD^b H^c$$

where V is the volume of the target individual tree, H is the height of the target individual tree, D is the diameter at breast height of the target individual tree, and a, b, and c are coefficients;

(3.5) computing the biomass by using the biomass expansion factor method, with the volume as an independent variable and the biomass as a dependent variable, and looking up tables to obtain three default data including a wood density, a root-crown ratio, and a biomass expansion factor, wherein a computational formula is as follows:

$$W = V \times WD \times BEF \times (1+R)$$

where WD is the wood density of the target individual tree, BEF is the biomass expansion factor that converts trunk biomass of the target individual tree to aboveground biomass and that is dimensionless, and R is the root-crown ratio of the target individual tree;

(3.6) converting forest biomass into the carbon storage by using a carbon content of forest biomass, and converting the carbon storage into a carbon dioxide equivalent, wherein a computational formula is as follows:

$$C_s = (44/12) \times W \times CF$$

where $C_s$ is the carbon storage of the target individual tree, and CF is the carbon content of the target individual tree;

(4) detecting state changes of the target individual tree, and performing step (6) if a monitoring state of the target individual tree changes, otherwise performing step (5);

(5) continuous monitoring of the target individual tree carbon sink: continuously receiving the data collected in step (2) at a set monitoring frequency and performing step (3), while storing the data;

(6) verification on the monitoring state of the target individual tree: verifying the state of the target individual tree on site, determining on site whether the monitoring state of the target individual tree changes due to equipment reasons or the state of the target individual tree changes, and performing step (1) if the monitoring state of the target individual tree changes due to equipment reasons and the monitoring continues, or ending the process if the state of the target individual tree changes or the monitoring does not continue.

2. The method for dynamic measurement of individual tree carbon sink according to claim 1, wherein specific steps of step (5) are as follows:

(5.1) the communication relay device is regularly started according to a set wake-up time;

(5.2) the communication relay device accesses a network server on a server side to obtain a next wake-up time and a wake-up duration;

(5.3) the tree diameter measuring sensor is regularly started according to a set wake-up time;

(5.4) the tree diameter measuring sensor measures the diameter at breast height of the target individual tree to obtain a measured value;

(5.5) the tree diameter measuring sensor is connected to the communication relay device to transmit information about the diameter at breast height, and a tilt angle of the target individual tree;

(5.6) the tree diameter measuring sensor synchronizes in clock with the communication relay device to obtain a next wake-up time and a wake-up duration, and enters a sleep state after success;

(5.7) the communication relay device receives data from the tree diameter measuring sensor for storage, and computes differences from previous measured data;

(5.8) the communication relay device computes a carbon storage variation according to a difference in tree diameter and stores the data;

(5.9) the communication relay device stores its own sensor data;

(5.10) the communication relay device transmits stored information back to a communication receiving device and summarizes the information into the network server on the server side;

(5.11) a compute server on the server side obtains data from the network server and summarizes carbon sink variations of individual trees for visual display;

(5.12) the server side configures a wake-up time and a wake-up duration of the communication relay device and a wake-up time and a wake-up duration of the tree diameter measuring sensor.

3. The method for dynamic measurement of individual tree carbon sink according to claim 2, wherein in step (4), if the communication relay device cannot receive measured data from the tree diameter measuring sensor, it is determined that the monitoring state of the target individual tree has changed.

4. The method for dynamic measurement of individual tree carbon sink according to claim 2, wherein specific steps of step (6) are as follows:

(6.1) reaching around the target individual tree, searching for the target individual tree according to survey information and a number plate, and performing step (6.2) if the target individual tree is found, or filling in reasons for the change in the monitoring state of the target individual tree at the data collection terminal if the target individual tree is not found, and ending the process;

(6.2) searching for and starting a communication gateway, filling in equipment reasons at the data collection terminal and performing steps (1) and (2) if the communication gateway is not found or fails to start, or performing step (6.3) if a state of the communication gateway is normal;

(6.3) searching for the target individual tree, filling in equipment reasons at the data collection terminal, installing a new tree diameter measuring sensor on a trunk of the target individual tree, and performing step (2).

5. The method for dynamic measurement of individual tree carbon sink according to claim 2, wherein the data collection terminal and the server side are deployed with a data collection application system and a system for dynamic measurement of individual tree carbon sink, wherein the data collection application system is configured to obtain server side information, connect the communication relay device and the tree diameter measuring sensor in a survey field to collect, enter and compute data, and manage configurations of the communication relay device and the tree diameter measuring sensor; and the system for dynamic measurement of individual tree carbon sink is configured for a manager to collect, count and visually analyze individual tree survey data obtained by the data collection terminal, and to manage parameter settings and operating states of all individual tree survey devices.

6. The method for dynamic measurement of individual tree carbon sink according to claim 5, wherein the system for dynamic measurement of individual tree carbon sink comprises:

a user login module: configured to log in to the system for dynamic measurement of individual tree carbon sink;

an individual tree map display, browse and query module: configured to provide interactive modes based on map operations and provide map operation functions comprising translation, zoom in, zoom out, hierarchical display, individual tree attribute information query, and individual tree coordinate positioning;

a survey table and default data configuration module: configured to configure a field tree survey attribute table, the tree height curve, the binary volume table, and default data;

a communication relay device equipment and state management module: configured to query an equipment number, equipment type and coordinate position of the communication relay device and number information of a sample plot, view an operating state, a battery capacity and a sensor measured data of the communication relay device, and configure a monitoring frequency, the wake-up time and the wake-up duration for the communication relay device;

a tree diameter measuring sensor equipment and state management module: configured to query an equipment number of the tree diameter measuring sensor and number information of individual trees, view an operating state, a battery capacity and a sensor measured data of the tree diameter measuring sensor, and configure the wake-up time and the wake-up duration for the tree diameter measuring sensor;

an individual tree carbon storage summarization and computation module: configured to summarize the data of the tree diameter measuring sensor transmitted back by each communication relay device through the communication receiving device, and compute a carbon storage result of an individual tree by using the tree height curve, the binary volume table, and the default data;

a carbon storage variation analysis module: configured to collect statistics on the summarized and computed individual tree data, analyze survey accuracy and carbon sink quantity, quality, structure and distribution output by region and type, and compare statuses of each monitoring object before and after a monitoring cycle, comprising output growth, consumption, and dynamic changes;

a carbon sink measurement result visual display module: configured to display monitoring data by using three-dimensional maps, visual charts, and time series axes, to intuitively reflect dynamic changes of monitoring results.

7. The method for dynamic measurement of individual tree carbon sink according to claim 6, wherein the data collection application system comprises:

a user login module: configured to log in to the data collection application system;

a map operation and positioning, navigation, track, and photography module: configured to provide interactive modes based on map operations and provide map operation functions comprising translation, zoom in, zoom out, hierarchical display, positioning, navigation, track collection, and photography;

a survey table and default data download module: configured to download and update the field tree survey attribute table, the tree height curve, the binary volume table, and the default data;

an individual tree field survey factor entry module: configured to enter basic information of project owners, project leaders and contacts, basic information of a project, basic information of a project forest land, and technical data information of the forest land;

a mobile communication signal testing module: configured to measure a type and strength of mobile signals in the survey field and communicate with a communication receiving end to test a success rate of signal transmission;

a communication relay device connection, testing and configuration module: configured to connect the data collection terminal with the communication relay device, set a data collection frequency, determine start-up time and start-up duration of the communication relay device and the tree diameter measuring sensor;

a tree diameter measuring sensor connection and data entry module: configured to connect the data collection terminal with the tree diameter measuring sensor and enter tree species of surveyed trees, a forest ownership certificate number, and forest area information after confirming a correct connection;

a tree diameter measuring sensor and communication relay device data transmission module: configured to trigger a background communication event between the tree diameter measuring sensor and the communication relay device after the information of the surveyed trees is entered, and transmit the equipment number, tree species, forest ownership certificate number, and forest area information from the tree diameter measuring sensor to the communication relay device through a wireless communication module for storage;

an individual tree carbon sink measurement module: configured to obtain tree survey data and then compute carbon storage by using the tree height curve, the binary volume table, and the default data.

* * * * *